(12) United States Patent
Zheng et al.

(10) Patent No.: US 10,111,763 B2
(45) Date of Patent: Oct. 30, 2018

(54) NON-CONTACT CAPACITIVE SENSING SYSTEM FOR ROBOTIC LOWER-LIMB PROSTHESIS

(71) Applicant: Peking University, Beijing (CN)

(72) Inventors: Enhao Zheng, Beijing (CN); Qining Wang, Beijing (CN); Kunlin Wei, Beijing (CN); Long Wang, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 14/771,136

(22) PCT Filed: May 9, 2014

(86) PCT No.: PCT/CN2014/000477
§ 371 (c)(1),
(2) Date: Aug. 27, 2015

(87) PCT Pub. No.: WO2015/149197
PCT Pub. Date: Oct. 8, 2015

(65) Prior Publication Data
US 2017/0007427 A1    Jan. 12, 2017

(30) Foreign Application Priority Data
Mar. 31, 2014  (CN) .......................... 2014 1 0125782

(51) Int. Cl.
*A61F 2/72* (2006.01)
*A61B 5/0488* (2006.01)
(Continued)

(52) U.S. Cl.
CPC .............. *A61F 2/72* (2013.01); *A61B 5/0492* (2013.01); *A61B 5/04888* (2013.01); *A61F 2/76* (2013.01);
(Continued)

(58) Field of Classification Search
CPC ...... A61F 2/72; A61F 2/7812; A61B 5/04888; A61B 5/0492
See application file for complete search history.

(56) References Cited

U.S. PATENT DOCUMENTS

| 4,445,189 A | * | 4/1984 | Hyatt | .................. B60R 16/0373 365/183 |
| 4,571,750 A | * | 2/1986 | Barry | ..................... A61B 7/006 600/586 |

(Continued)

*Primary Examiner* — Bruce E Snow
*Assistant Examiner* — Melissa Hoban
(74) *Attorney, Agent, or Firm* — McCoy Russell LLP

(57) ABSTRACT

A non-contact capacitive sensing system for robotic lower-limb prosthesis, comprising a sensing front end, a signal sampling unit and a signal processing unit. The sensing front end is composed of capacitance electrodes inside the prosthetic socket, and the capacitance electrodes locate between the prosthetic socket and the stump sock. Each capacitance electrode forms a capacitor with the human body. The signal sampling unit is composed of the CTD module and the control module. The CTD module measures capacitance values by calculating the ratio of discharge-and-recharge cycles between the under-test capacitors and the reference capacitor. The signal processing unit comprises the filter module and the communication module. The capacitive sensing system is highly repeatable in signals, resistant to sweat, and reliably dressed on a human body. The system performs well regardless of residual limb length and residual muscle strength. It can be widely used in the field of robotic lower-limb prosthesis.

18 Claims, 3 Drawing Sheets

(51) Int. Cl.
*A61B 5/0492* (2006.01)
*A61F 2/76* (2006.01)
*A61F 2/78* (2006.01)
*A61F 2/80* (2006.01)

(52) U.S. Cl.
CPC .............. *A61F 2/7812* (2013.01); *A61F 2/80* (2013.01); *A61F 2002/7615* (2013.01)

(56) References Cited

U.S. PATENT DOCUMENTS 6,185,452 B1 * 2/2001 Schulman ............ A61B 5/0031
 604/20
8,591,599 B1 * 11/2013 Kaliki .................. A61B 5/6828
 600/372

* cited by examiner

NON-CONTACT CAPACITIVE SENSING SYSTEM FOR ROBOTIC LOWER-LIMB PROSTHESIS

CROSS REFERENCE TO RELATED APPLICATIONS

The present application is a U.S. National Phase of International Patent Application Serial No. PCT/CN2014/000477, entitled "A NON-CONTACT CAPACITIVE SENSING SYSTEM FOR ROBOTIC LOWER-LIMB PROSTHESIS," filed on May 9, 2014, which claims priority to Chinese Patent Application Serial No. 201410125782.1, entitled "A NON-CONTACT CAPACITIVE SENSING SYSTEM FOR ROBOTIC LOWER-LIMB PROSTHESIS," filed on Mar. 31, 2014, the entire contents of each of which are hereby incorporated by reference for all purposes.

FIELD OF THE INVENTION

The invention relates to a non-contact capacitive sensing system in the field of robotic lower-limb prosthesis, and more particularly, to a non-contact capacitive sensing system for locomotion mode recognition to control the robotic transtibial prosthesis.

BACKGROUND OF THE INVENTION

Robotic lower-limb prosthesis is an emerging technology which has been developed since the decades from the end of the 20th century to the beginning of the 21st century. Robotic lower-limb prosthesis is usually equipped with the specialized control system and the particularly designed mechanical structure. These characteristics allow it to accurately mimic human joint angle curves and to restore the joint torques during ambulation, both of which greatly extents the walking ability of the lower extremity amputees. At the current stage, the most common control strategy for the robotic prosthesis is the hierarchical control, wherein the high level controller recognizes the locomotion modes on different terrains such as level walking, stair ascending, etc. The middle level controller derivates the angle curves and the torque curves based on the corresponding locomotion mode. The low level controller drives the actuation system (including motors, hydraulic system, and pneumatic system) to achieve the human joint dynamics.

The sensing system and sensing strategy are crucial for accurate and timely recognition of human motion information, which is the primary goal of the hierarchical control system. At the current stage of this field, the most widely applied technology is the surface electromyography (sEMG) based sensing system. The sEMG signal exhibits short time latency and accurate motion information, as it directly records muscle contraction information. However, in the application of lower-limb prosthesis, there exist some limitations using sEMG sensing systems. First, in order to record useful muscle signals, the sEMG electrode has to be placed at the position of the measured muscle. Due to the amputation, the muscle loss on the limb and the residual muscle atrophy make it difficult to sample enough channels of sEMG signals. Second, the sEMG electrodes are tightly adhered to the skin, and thereby the pressures on the sensing spots made by the electrodes will cause skin damage and pressure sores, especially in long time use. Meanwhile, the sweats impact on the signal quality and decrease the system's performance. Third, sEMG signal is weak in magnitude (dozens of microvolt) and the valid frequency ranges from several Hz to 1 kHz. To digitally sample the signals, multi-stage amplifiers and filters are needed in the sampling circuits. The complication of the sampling circuits increases the cost of the whole system, especially for multi-channel sampling.

At present, the current capacitive sensing technology for recognizing locomotion modes records the muscle shape changes on the leg based on the particularly designed sensing bands. This technology is a potential alternative to EMG based system in locomotion mode recognition, and it is promising in applications of exoskeleton control and human motion detection. However, for lower-limb prosthesis, there exist some limitations. First, the electrodes on the sensing bands directly contact with the skin, in which condition, the sweats still potentially impacts on the performance. Second, the electrode positions have to be configured each time re-wearing the bands, which increase the inconvenience in daily application. Third, for lower extremity amputees, sensing bands cannot be placed inside the socket. As a result, for transtibial amputees, only the band on the thigh can be used, and the transfemoral amputees cannot use it due to the limited residual limb length.

SUMMARY OF THE INVENTION

To overcome the above-mentioned drawbacks, the invention provides a non-contact capacitive sensing system for robotic transtibial prosthesis. The first objective of the invention is to provide a non-contact capacitive sensing system which is highly repeatable in signals, immune to influence of sweats, reliably dressed on human body, and low cost. The second objective of the invention is to provide a non-contact capacitive sensing system which performs well regardless of the residual limb length of the amputees.

To achieve the objectives, the invention is realized with the following technical schemes.

A non-contact capacitive sensing system for robotic lower-limb prosthesis, which is characterized by:

the system comprises the sensing front end, signal sampling unit and signal processing unit;

the sensing front end is configured to form the coupling capacitors with human body; the signal sampling unit is configured to convert the raw capacitance signals to digital signals;

the signal processing unit is configured to firstly regulate the digital signals sampled by the signal sampling unit and then transmit the regulated signals to the subsequent processors.

More particularly, the sensing front end comprises capacitance electrodes each of which represents one signal channel. Each capacitance electrode is fixed between the prosthetic socket and the stump sock, forming a coupling capacitor together with human body. The capacitance electrodes are placed inside the prosthetic socket, being fixed on the outer surface of the stump sock by doubles-side conductive adhesive tapes and insulated from the socket by insulated tapes. The capacitance electrodes are connected to the signal sampling unit via shielding lines. The signal sampling unit described above comprises a capacitance-to-digital (CTD) module and a control module, where the CTD module contains a reference capacitor and records the discharge-and-recharge cycle time for both the coupling capacitors under test and the reference capacitor. After receiving the time values, the control module calculates the capacitance values of the under-test coupling capacitors based on the ratio of the discharge-and-recharge cycle time between the coupling capacitors and the reference capacitor.

The results are transmitted to the subsequent signal processing unit. The signal processing unit is composed of a digital filter module and a communication module, where, the digital filter module is used to remove the noises in the capacitance signals, and the communication module is used to wirelessly transmit the filtered data to the subsequent processors.

According to an embodiment of the invention, the electrodes are made of copper meshes.

The channel number of the capacitance electrodes is optimized as six. The sensing positions of the capacitance electrodes on human body comprise the downside of the mid patella-tendon, the distal end of the residual tibia, the residual gastrocnemius muscle, the posterior of the distal end, the medial side of the thighbone (on the knee joint) and the lateral side of the thighbone (on the knee joint).

The CTD module comprises a strobe, a Schmidt trigger and a calculator. The strobe connects the coupling capacitors and the reference capacitor to the Schmidt trigger in the time-sharing way. The Schmidt trigger converts the capacitive discharge-and-recharge curve to the square wave. The calculator accumulates the duration of each cycle of the square wave and then calculates the capacitance values.

According to an embodiment of the invention, the CTD module is connected with the processing module via serial peripheral interface (SPI) bus.

According to an embodiment of the invention, the digital filter module as described above is implemented on a micro control unit STM32 (STMicroelectrionics Co. Ltd.).

The digital filter module comprises filters of three stages. The first stage filter is the median filter, and the second stage filter is the 1st order direct current (DC) notch filter, and the third stage is the 2nd order Butterworth low pass filter.

More particularly, in the median filter, a window of N samples slides across the raw data, and the median value of the window is set to be the current filtered data.

In the 1st order direct current (DC) notch filter, the transfer function is expressed as:

$$H(z) = \beta \frac{1 - z^{-1}}{1 + \alpha z^{-1}},$$

where, $\alpha$ determines the frequency characteristics of the filter, and $\beta$ determines the gain of the filter.

According to an embodiment of the invention, the communication module as described above is implemented with the communication micro ship nRF24L01 (Nordic Co. Ltd.). The maximum data rate is 2 MHZ, and the communication with MCU is realized with SPI bus.

Due to the technical schemes described above, there are several advantages in the invention. First, the sensing front end of the invention combines the capacitance electrodes in the prosthetic socket with human body to form coupling capacitors. The leg volume changes caused by residual muscle contraction and the interface force between the residual limb and the socket lead to the capacitance value changes. The non-contact way of dressing on human body also avoids the influence of the sweats. Meanwhile, the copper-mesh-made electrodes are thin and flexible and have no extra pressures on the sensing spots that negatively influence the ambulation. Second, a CTD module is implemented in the signal sampling unit. The CTD module computes the capacitance values by recording the discharge-and-recharge time of the capacitors, the resolution of which is as high as several fF. The sampling scheme used in the invention directly converts the capacitance to digital signal, which avoids the problems in multi-stage amplification method. Third, the filter module in the signal processing unit is designed with a three-stage filter. The second stage filter is 1st order DC notch filter which can effectively remove the baseline drifting caused by temperature change. Moreover, the DC notch filter yields smaller signal distortion than the high pass filter and the band pass filter at the capacitance signal frequency band. Therefore, the filtered signals are with high fidelity and repeatability. Finally, four of the sensing positions as described above locate in the sagittal plane and the rest two locate at the both sides of the knee joint. By this way, locomotion information is fully extracted. The invention can be widely applied in lower-limb prosthesis.

BRIEF DESCRIPTION OF THE DRAWINGS

The accompanying drawings are included to provide a further understanding of the invention. The drawings illustrate embodiments of the invention and, together with the description, serve to explain the principles of the invention.

DESCRIPTION OF THE EMBODIMENTS

The invention provides a sensing system based on the principle of capacitance sensing. The electrodes are placed inside the prosthetic socket and couples with human body to form capacitors. The capacitance signals convey the human motion information which is used to recognize locomotion modes. The non-contact capacitive sensing system belongs to the high level controller in the hierarchical control strategy in robotic lower-limb prosthesis, whose purpose is to recognize locomotion modes and to provide motion information to the lower controllers.

Description will now be made in detail on the preferred embodiments of the invention, examples of which are illustrated in the accompanying drawings.

Figure 1:
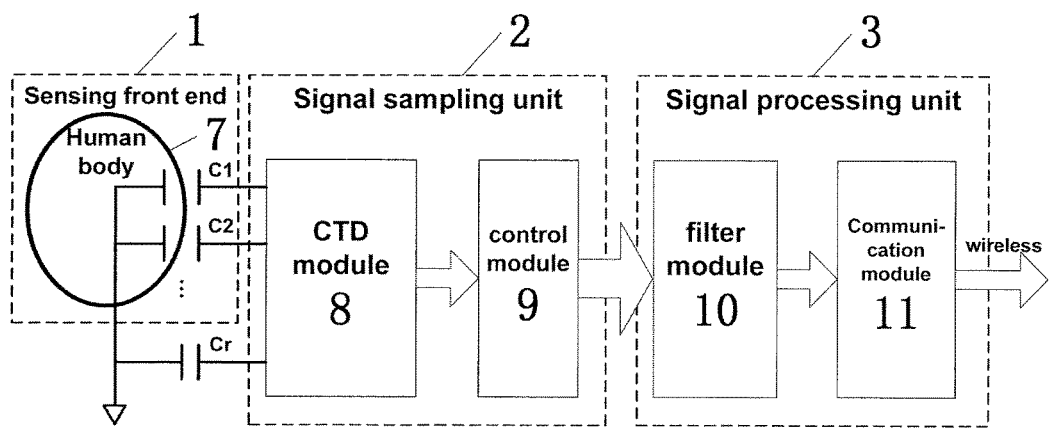
FIG. 1 shows the block diagram of the non-contact capacitive sensing system according to an embodiment of the invention.

FIG. 1 is the block diagram of the non-contact capacitive sensing system. The preferred embodiment of the invention comprises the sensing front end 1, signal sampling unit 2, and signal processing unit 3. The sensing front end 1 is used to form the coupling capacitors with human body. The signal sampling unit 2 is used to convert the capacitance values to digital signals. The signal processing unit 3 processes the signals sampled by the signal sampling unit 2 and transmits the filtered data to the subsequent processors. The subsequent processing algorithms will provide human motion intent information for prosthesis control.

Figure 2:
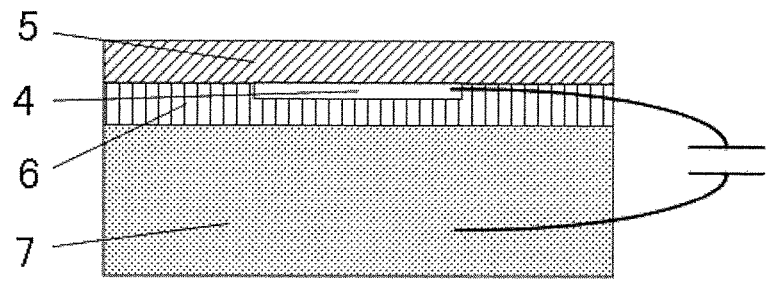
FIG. 2 shows the sensing principle of a coupling capacitor according to an embodiment of the invention.

As shown in FIG. 2, the sensing front end 1 in the preferred embodiment is composed of multi-channel capacitance electrodes each of which is like 4. Each electrode is fixed between the prosthetic socket 5 and stump sock 6, coupling with human body 7 to form a capacitors $C_i$ (i=1, 2, 3 . . . ). The number of the coupling capacitors $C_i$ is adjusted based on the type of the amputation. More particularly, each capacitance electrode 4 is placed inside the prosthetic socket 5 and is adhered to the outer surface of the stump sock 6, which makes the electrode non-contact with human skin. Each electrode 4 is insulated from the inner surface of the prosthetic socket 5 by insulated tapes. Each electrode 4 is connected to the signal sampling unit 2 with the shielding line.

According to the preferred embodiment of the invention, the stump sock 6 is the dielectric of the coupling capacitors. The material of the stump sock 6 is depends on the choice of the amputees. Most of the amputees use silicon-made sock as their stump socks. Some of the amputees wear additional socks inside the stump sock 6, as their residual limb muscles no longer fitted their sockets after long time use. In the preferred embodiment of the invention, the amputee wears a layer of sock which is made from nylon. During locomotion, the residual muscle volume changes caused by muscle contraction and the interface force between residual limb and the prosthetic socket 5 both give rise to the gap changes between the human body and the electrode 4. The gap changes are subsequently reflected by the capacitance values.

Figure 3:
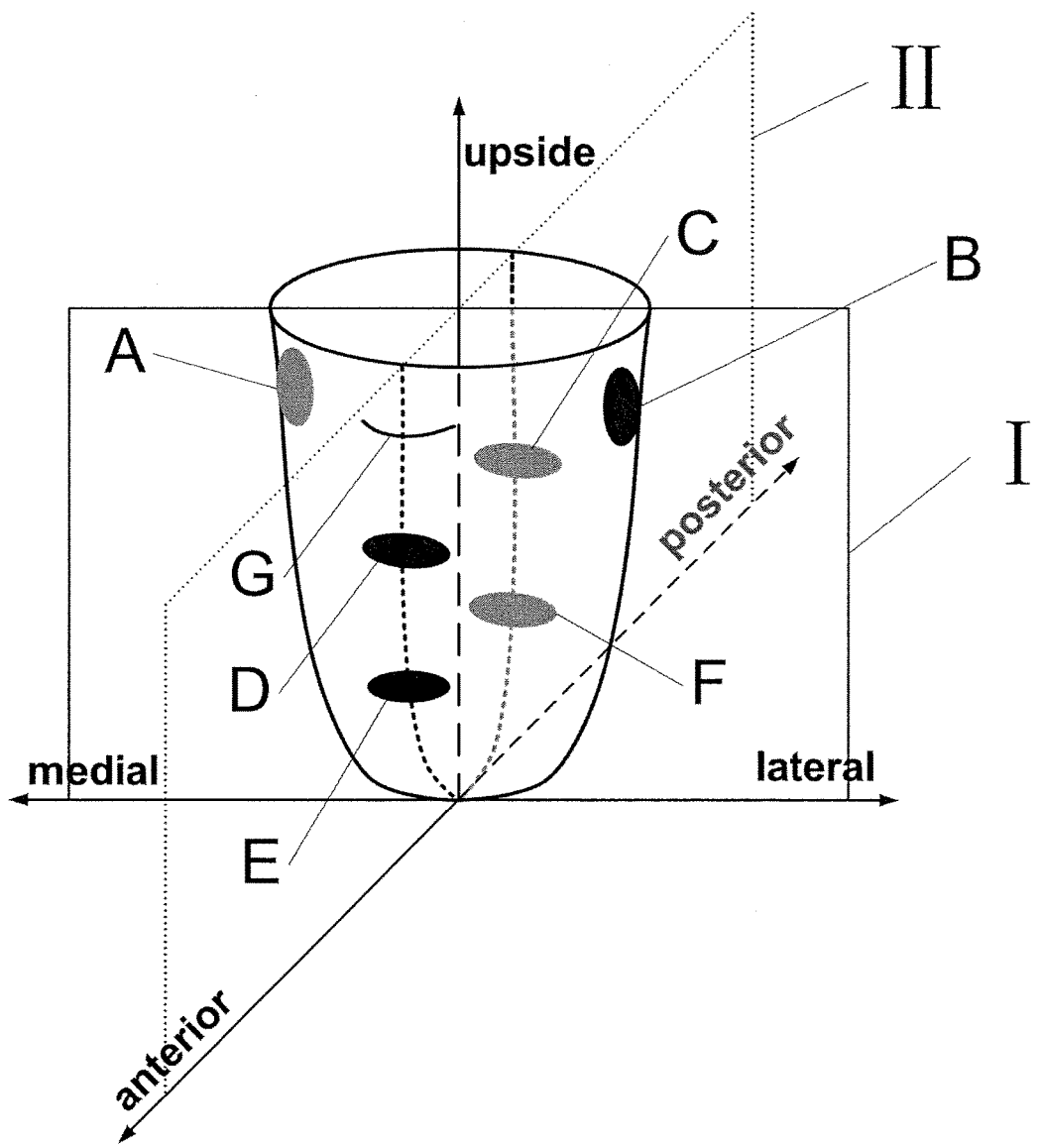
FIG. 3 shows the schematic diagram of the sensing positions of the capacitance electrodes in the prosthetic socket according to an embodiment of the invention.
Figure 5:
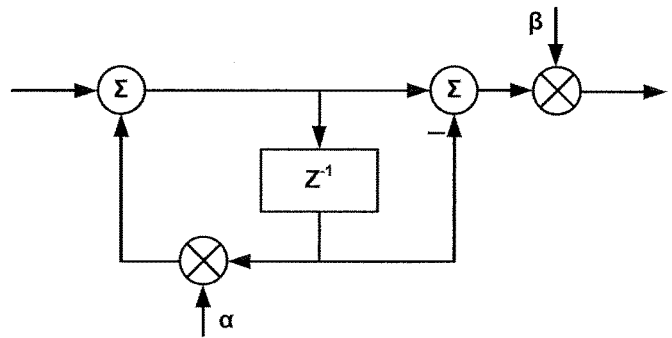
FIG. 5 shows the block diagram of the 1st order DC notch filter according to an embodiment of the invention.

According to the preferred embodiment of the invention, each capacitance electrode 4 is made of copper mesh, the size of which is determined based on the residual limb length of the amputee in practical use. In the preferred embodiment, the residual limb length ratio of the amputee is 32%, and the thickness of the capacitance electrode 4 is 0.1 mm, and the size is 3.5 cm×4 cm. In the preferred embodiment, the sensing positions of the capacitance electrodes 4 on the left-leg prosthetic socket are shown in FIG. 3. The sensing positions of the capacitance electrodes (from channel A to channel F) on the left leg comprise 1. the downside of the mid patella-tendon, 2. the distal end of the residual tibia, 3. the posterior of the distal end, 4. the residual gastrocnemius muscle, 5. the medial side of the thighbone (on the knee joint) and 6. the lateral side of the thighbone (on the knee joint). More particularly, the sensing positions from channel A to channel F are listed as follows. The electrodes of channel A and channel B are located in the coronal plane I, being placed on the lateral side and the medial side of the thighbone (the knee joint). The electrodes 4 of channel D and channel E are placed in the anterior part of the sagittal plane II, being on the downside of the mid patella-tendon and the distal end of the residual tibia, respectively. The electrodes 4 of channel C and channel F are placed on the posterior part of the sagittal plane II, and more particularly, on the distal end and the residual gastrocnemius muscle. Since most of the locomotion modes take place in the sagittal plane I, the four electrodes in the plane record most of the human motion information. The electrodes 4 in the coronal plane are placed on both sides of the thighbone. The ligaments of the knee joint G are intact for transtibal amputees. The muscle contractions of the knee joint during knee flexion and extension are recorded using the two electrodes 4.

According to the preferred embodiment of the invention, the signal sampling unit 2 is composed of the CTD module 8 and the control module 9, wherein the CTD module 8 comprises a reference capacitor $C_r$, based on which the CTD module 8 sets the value of the discharging resistor and the counter clock. The CTD module 8 measures the discharge-and-recharge time of the coupling capacitor under test $C_i$ and the reference capacitor $C_r$. The digitalized capacitance signals are then sent to the control module 9. The function of the control module 9 is to calculate the value of the under-test coupling capacitor based on the ratio of the discharge-and-recharge time between the under-test coupling capacitor $C_i$ and the reference capacitor $C_r$. The calculated capacitance values are then sent to the signal processing unit 3. The communication protocol is determined based on the sampling rate of the signal sampling unit 2. In the preferred embodiment of the invention, the sampling rate is 100 Hz, in other words, the capacitance signals are updated in each 10 ms.

Figure 4:
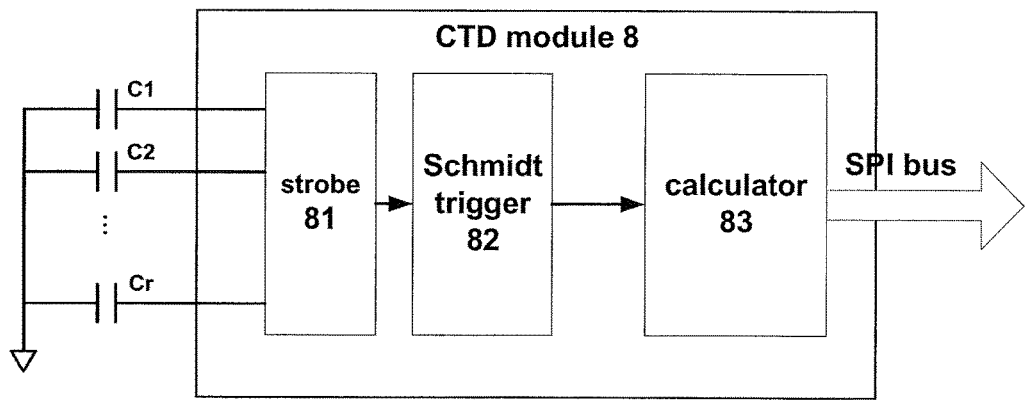
FIG. 4 shows the block diagram of the CTD module according to an embodiment of the invention.

In the preferred embodiment of the invention, the CTD module 8 is composed of the strobe 81, the Schmidt trigger 82 and the calculator 83, as shown in FIG. 4. The strobe 81 connects each coupling capacitor and the reference capacitor in a time-sharing way. In each time slice, the reference capacitor and an under-test coupling capacitor are connected to the Schmidt trigger 82. The Schmidt trigger 82 transforms the charging-and-discharging capacitance signal curve to square wave. The calculator 83 calculates the time of the cycle, which is the digitalized capacitance signal. The calculator 83 uses averaging filter to remove the random noises. In the preferred embodiment of the invention, the number of the average is optimized as 10.

In the preferred embodiment of the invention, the communication protocol between the CTD module 8 and the control module 9 is the SPI bus.

In the preferred embodiment of the invention, the capacitors in the sensing front end 1 share a discharging resistor. In the CTD module 8, one pole of the reference capacitor $C_r$ and the circuit ground are connected with the human body. The value of the under-test coupling capacitor is influenced by both the area of the electrode 4 and the material of the stump sock 6. To make the reference capacitor and the under-test capacitors stay in the same level, the value of the reference capacitor $C_r$ is determined through experiment trials. In the preferred embodiment, the circuit ground is connected to a piece of conductive fiber being fixed on the inner surface of the stump sock. Direct wearing of the stump sock on the residual limb makes the ground of the CTD module adhere to the human skin. The reference capacitance is 100 pF in the preferred embodiment of the invention. The discharging resistor is calculated by the function:

$$V_t = V_0 e^{-ti/RC}$$

where, $V_0$ is the initial voltage on the reference capacitor, and $V_t$ is the voltage at time t. In the preferred embodiment of the invention, the CTD module 8 pre-defines $V_0$ and $V_t$. The discharging time t is recorded by the counter in the control module 9. There is a trade-off between the resolution and the sampling rate. The sampling rate is 100 Hz as mentioned above, and the counter clock frequency of the control module 9 is 48 MHz. By compromising between the sampling rate and the resolution, the discharging resistor is 180 KΩ.

In the invention, the signal processing unit 3 is composed of digital filter module 10 and the communication module 11. The digital filter module 10 is used to remove the noises in the raw capacitance signals and to transmit the filtered data to the communication module 11.

According to the preferred embodiment of the invention, the digital filter module 10 is implemented on the STM 32 (STMicroelectrionics Co. Ltd.) microchip. The digital filter module 10 is a three-stage filter, wherein, the first stage is median filter, the second stage is the $1^{st}$-order DC notch filter, and the third stage is the $2^{nd}$-order Butterworth low band pass filter. The communication module 11 is used to send the data to the subsequent processing devices.

More particularly, the median filter replaces the raw data with the median value of a sliding window. In the preferred embodiment of the invention, the sliding window length is optimized as four samples. The median filter removes the random pulses in the raw signals.

The transfer function of the $1^{st}$-order DC notch filter is expressed as:

$$H(z) = \beta \frac{1-z^{-1}}{1+\alpha z^{-1}},$$

where, $\alpha$ determines the frequency characteristics of the filter, and $\beta$ determines the gain of the filter. In the preferred embodiment of the invention, $\beta$ is optimized as 0.95 and $\beta$ is 2.5. In signal sampling procedure, the temperature influences capacitance value and causes baseline drifting. If using high band pass filter to remove the baseline drifting, the signal components near cut-off frequency will be influenced. Since the useful frequency in the field of the invention is smaller than 10 Hz, the signal distortion will decrease the recognition performance of the non-contact capacitive sensing system. By comparison, the $1^{st}$-order DC notch filter in the invention perfectly removes the signal drifting without losing useful information.

The $2^{nd}$-order low band pass Butterworth filter is used to remove the high frequency noises. In the preferred embodiment of the invention, the cut-off frequency is set as 10 Hz.

In the preferred embodiment of the invention, the communication module 11 adopts the communication microchip nRF24L01 (Nordic Co. Ltd.). The maximum of the wireless data rate is 2 MHz and it communicates with the control module 6 via SPI bus. In the embodiment, the re-transmission strategy is adopted to guarantee the stability of the communication, which operates in such a way that, after the transmission of a data packet, the receiver sends back a Cyclic Redundancy Check (CRC) data, and if the CRC data is different from the one on the transmitter, the data packet will transmitted once more. In the preferred embodiment of the invention, the maximum re-transmission time is set as 5.

In order to validate the preferred embodiments of the invention, an experiment measuring different locomotion modes of an amputee was carried out. The height of the amputee was 170 cm, and the weight being 71 kg. The amputee's left shank had been amputated for eight years by the time of the experiment. During the experiment, the amputee was asked to wear his own prosthesis, and the capacitance electrodes 4 were fixed inside his prosthetic socket as described above. A foot pressure insole was also placed in the shoe of the amputated side to record the foot-contact event and the foot-off event. The amputee was asked to perform five locomotion modes which encountered frequently in daily life, including level walking, stair ascending, stair descending, ramp ascending and ramp descending. There were ten groups of measurement in the experiment. In each group, data of two trials on each locomotion mode were recorded. In each trial, the amputee ambulated for at least two strides. In order to make the experiments similar to real life, the amputee was asked to alternatively perform the locomotion modes with his own pace.

Figure 6:
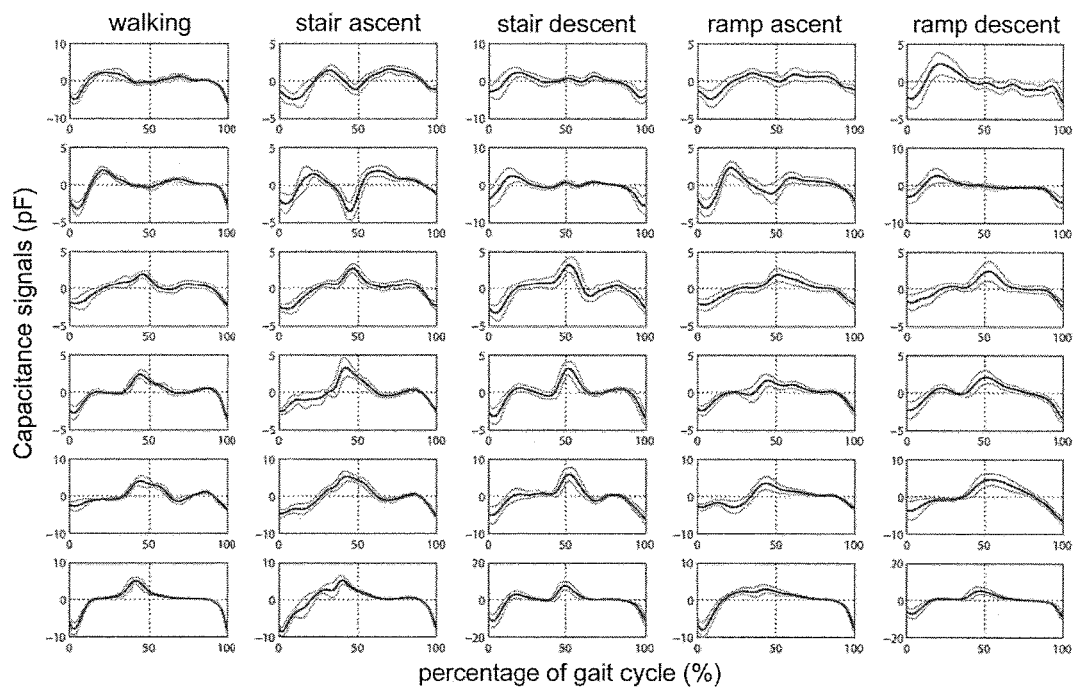
FIG. 6 shows the signals of the system measured in an embodiment of the invention.

As shown in FIG. 6, the axis x denotes the percentage of the gait cycle. The axis y represents the capacitance values. In each subfigure, the bold line represents the average signal and the fine line represents the standard deviation. Each column stands for a locomotion mode and the each row stands for a capacitance signal. In the experiment, data of 20 gait cycles for each locomotion mode are acquired. The signals are time-normalized according to the percentage of one gait cycle, and thereby the average values and the standard deviations are calculated across all the gait cycles. It can be seen from FIG. 6 that the non-contact capacitive sensing system produces high repeatability in the same locomotion mode. The signals of different locomotion modes are also clearly distinguishable.

The preferred embodiments of the invention proves that the non-contact capacitive sensing system provided by the invention not only overcomes the drawbacks of the current technologies (the EMG-based sensing system and the existing capacitive sensing system for human motion measurement) but also accurately records the capacitance signals of an amputee on different locomotion modes. The system satisfies the requirements of locomotion mode recognition for robotic prosthesis.

The embodiments that have been described above are merely illustrative of and not restrictive on the broad invention. It will be understood to those skilled in the art that various modifications can be made to the structure, operation method and manufacture of the invention without departing from the scope or spirit of the invention. Accordingly, the invention covers the modifications and variations of this invention that fall within the scope of the claims.

The invention claimed is:

1. A non-contact capacitive sensing system for a robotic prosthesis, comprising: a sensing front end configured to form coupling capacitors with a human body; a signal sampling unit configured to convert capacitance values of the coupling capacitors to digitalized capacitance signals; and a signal processing unit configured to regulate the digitalized capacitance signals sampled by the signal sampling unit and transmit the regulated digitalized capacitance signals to subsequent processors;

wherein the sensing front end is composed of capacitance electrodes with multi channels, each of which is placed between a prosthetic socket and a stump sock and is configured to couple with the human body to form the coupling capacitors; the capacitance electrodes are adhered to an outer surface of the stump sock and insulated from an inner surface of the prosthetic socket with insulated tapes and all electrodes are connected to the signal sampling unit with shielding lines;

wherein the signal sampling unit comprises a capacitance-to-digital (CTD) module disposed over a reference capacitor and a control module; wherein the CTD module is configured to measure a charge-and-recharge cycle time of the reference capacitor and the coupling capacitors under test, and transmit a value to the control module; the control module is configured to calculate under-test capacitance values based on a ratio of charge-and-recharge cycle between the reference capacitor and the coupling capacitors under test, and transmit the capacitance value to the signal processing unit; and wherein the signal processing unit comprises a digital filter module and a communication module; the digital filter module is configured to remove noises in the capacitance value to obtain filtered data; the communication module is configured to transmit the filtered data to the subsequent processors.

2. The non-contact capacitive sensing system of the robotic prosthesis of claim 1, wherein each capacitance electrode is made of copper mesh.

3. The non-contact capacitive sensing system of the robotic prosthesis of claim 2, wherein a number of the capacitance electrodes is optimized as six, and sensing positions on a leg of the human body respond to a downside of a mid patella-tendon, a distal end of a residual tibia, a posterior of the distal end, a residual gastrocnemius muscle, a medial side of a thighbone (on a knee joint) and a lateral side of the thighbone (on the knee joint).

4. The non-contact capacitive sensing system of the robotic prosthesis of claim 2, wherein the CTD module comprises a strobe, a Schmidt trigger, and a calculator; the strobe is configured to connect under-test capacitors with the Schmidt trigger in a time-sharing way; the Schmidt trigger is configured to convert a capacitive charge-and-discharge curve to a square wave; the calculator is configured to calculate a duration of a cycle of the square wave and obtain the digitalized capacitance signals.

5. The non-contact capacitive sensing system of the robotic prosthesis of claim 2, wherein communication between the CTD module and the control module is implemented with an SPI bus.

6. The non-contact capacitive sensing system of the robotic prosthesis of claim 2, wherein the digital filter module is composed of three stages of filters, a first stage being a median filter, a second stage being a $1^{st}$ order DC notch filter, and a third stage being a $2^{nd}$ order low band pass Butterworth filter.

7. The non-contact capacitive sensing system of the robotic prosthesis of claim 1, wherein a number of the capacitance electrodes is optimized as six, and sensing positions on a leg of the human body respond to a downside of a mid patella-tendon, a distal end of a residual tibia, a posterior of the distal end, a residual gastrocnemius muscle, a medial side of a thighbone (on a knee joint) and a lateral side of the thighbone (on the knee joint).

8. The non-contact capacitive sensing system of the robotic prosthesis of claim 7, wherein the CTD module comprises a strobe, a Schmidt trigger, and a calculator; the strobe is configured to connect under-test capacitors with the Schmidt trigger in a time-sharing way; the Schmidt trigger is configured to convert a capacitive charge-and-discharge curve to a square wave; the calculator is configured to calculate a duration of a cycle of the square wave and obtain the digitalized capacitance signals.

9. The non-contact capacitive sensing system of the robotic prosthesis of claim 7, wherein communication between the CTD module and the control module is implemented with an SPI bus.

10. The non-contact capacitive sensing system of the robotic prosthesis of claim 7, wherein the digital filter is composed of three stages of filters, a first stage being a median filter, a second stage being a $1^{st}$ order DC notch filter and a third stage being a $2^{nd}$ order low band pass Butterworth filter.

11. The non-contact capacitive sensing system of the robotic prosthesis of claim 1, wherein the CTD module comprises a strobe, a Schmidt trigger, and a calculator; wherein the strobe is configured to connect under-test capacitors with the Schmidt trigger in a time-sharing way; the Schmidt trigger is configured to convert a capacitive charge-and-discharge curve to a square wave; the calculator is configured to calculate a duration of a cycle of the square wave and obtain the digitalized capacitance signals.

12. The non-contact capacitive sensing system of the robotic prosthesis of claim 11, wherein the digital filter module is composed of three stages of filters, a first stage being a median filter, a second stage being a $1^{st}$ order DC notch filter, and a third stage being a $2^{nd}$ order low band pass Butterworth filter.

13. The non-contact capacitive sensing system of the robotic prosthesis of claim 1, wherein communication between the CTD module and the control module is implemented with an SPI bus.

14. The non-contact capacitive sensing system of the robotic prosthesis of claim 13, wherein the digital filter module is composed of three stages of filters, a first stage being a median filter, a second stage being a $1^{st}$ order DC notch filter, and a third stage being a $2^{nd}$ order low band pass Butterworth filter.

15. The non-contact capacitive sensing system of the robotic prosthesis of claim 1, wherein the digital filter module is composed of three stages of filters, a first stage being a median filter, a second stage being a $1^{st}$ order DC notch filter, and a third stage being a $2^{nd}$ order low band pass Butterworth filter.

16. The non-contact capacitive sensing system of the robotic prosthesis of claim 15, wherein the median filter is configured to calculate a median value of an N-length window as a current value.

17. The non-contact capacitive sensing system of the robotic prosthesis of claim 15, wherein a transfer function of the $1^{st}$ order DC notch filter is expressed as:

$$H(z) = \beta \frac{1 - z^{-1}}{1 + \alpha z^{-1}},$$

where, $\alpha$ determines frequency characteristics of the filter, and $\beta$ determines a gain of the filter.

18. The non-contact capacitive sensing system of the robotic prosthesis of claim 1, wherein the communication module is implemented with a microchip which has a maximum wireless data rate of 2 MHz; wherein it communicates with the digital filter module via an SPI bus.

* * * * *